United States Patent
Allen et al.

(10) Patent No.: US 10,692,623 B2
(45) Date of Patent: Jun. 23, 2020

(54) APPARATUS AND METHOD OF FORMING AN APPARATUS COMPRISING TWO DIMENSIONAL MATERIAL

(71) Applicant: Nokia Technologies Oy, Espoo (FI)

(72) Inventors: Mark Allen, Great Cambourne (GB); Zoran Radivojevic, Cambridge (GB); Christopher Bower, Cambridge (GB)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 16/075,417

(22) PCT Filed: Feb. 14, 2017

(86) PCT No.: PCT/FI2017/050084
§ 371 (c)(1),
(2) Date: Aug. 3, 2018

(87) PCT Pub. No.: WO2017/140944
PCT Pub. Date: Aug. 24, 2017

(65) Prior Publication Data
US 2019/0088382 A1    Mar. 21, 2019

(30) Foreign Application Priority Data
Feb. 15, 2016   (EP) .................................... 16155639

(51) Int. Cl.
*H01B 1/04*   (2006.01)
*D03D 1/00*   (2006.01)
(Continued)

(52) U.S. Cl.
CPC ............. *H01B 1/04* (2013.01); *A61B 5/6804* (2013.01); *B82Y 40/00* (2013.01); *D03D 1/0088* (2013.01); *D03D 15/00* (2013.01); *D10B 2401/16* (2013.01)

(58) Field of Classification Search
CPC ........ H01B 1/04; D03D 1/0088; D03D 15/00; B82Y 40/00
(Continued)

(56) References Cited

U.S. PATENT DOCUMENTS

| 3,864,160 A * | 2/1975 | Davidoff ................. D06Q 1/04 |
| | | 428/196 |
| 6,687,523 B1 | 2/2004 | Jayaramen et al. |
| 8,107,153 B2 | 1/2012 | Sotzing et al. |
| 2011/0211313 A1* | 9/2011 | Ward .................... H01L 23/373 |
| | | 361/704 |

(Continued)

FOREIGN PATENT DOCUMENTS

| CN | 103966844 A | 8/2014 |
| CN | 104674541 A | 6/2015 |

(Continued)

OTHER PUBLICATIONS

Suk "Transfer of CVD-Grown Monolayer Graphene onto Arbitrary Substrates." ACSNano,5(9),pp. 6916-6924 (Year: 2011).*

(Continued)

*Primary Examiner* — Tri V Nguyen
(74) *Attorney, Agent, or Firm* — Harrington & Smith

(57) ABSTRACT

A method and apparatus, the method comprising: transferring a layer of two dimensional material from a liquid surface onto a layer of woven electronic fabric; wherein the woven electronic fabric comprises a plurality of conductive strands and a plurality of non conductive strands such that the layer of two dimensional material and woven electronic fabric form a sensor.

13 Claims, 13 Drawing Sheets

(51) Int. Cl.
  *D03D 15/00* (2006.01)
  *B82Y 40/00* (2011.01)
  *A61B 5/00* (2006.01)
(58) Field of Classification Search
  USPC ..... 252/500, 502, 506, 510, 511; 423/445 R, 423/460
  See application file for complete search history.

(56) References Cited

U.S. PATENT DOCUMENTS

| | | | |
|---|---|---|---|
| 2014/0177178 A1* | 6/2014 | Crain | C09D 7/70 361/748 |
| 2015/0132565 A1 | 5/2015 | McKay et al. | |
| 2018/0195210 A1* | 7/2018 | Sunshine | D02G 3/441 |

FOREIGN PATENT DOCUMENTS

| | | |
|---|---|---|
| EP | 2784198 A1 | 10/2014 |
| EP | 3070741 A1 | 9/2016 |
| EP | 3163296 A1 | 5/2017 |
| EP | 3211660 A1 | 8/2017 |
| WO | 2007/093947 A1 | 8/2007 |
| WO | 2011/163556 | 12/2011 |

OTHER PUBLICATIONS

Lv et al., "High Carrier Mobility in Suspended-Channel Graphene Field Effect Transistors", Applied Physics Letters, vol. 103, No. 19, 2013, 4 pages.

Konstantatos et al., "Hybrid Graphene—Quantum Dot Phototransistors with Ultrahigh Gain", Nature Nanotechnology, vol. 7, Jun. 2012, pp. 363-368.

Li et al., "Multifunctional Graphene Woven Fabrics", Scientific Reports, vol. 2, Article No. 395, May 4, 2012, pp. 1-8.

"Conductive Graphene Yarn is Lighter and Stretchier Than Copper Wire", New Atlas, Retrieved on Jul. 31, 2018, Webpage available at : https://newatlas.com/stretchable-graphene-yarn/32657/.

Lee et al., "Flexible Graphene Woven Fabrics for Touch Sensing", Applied Physics Letters, vol. 102, No. 16, Apr. 25, 2013, 5 pages.

Neves et al., "Transparent Conductive Graphene Textile Fibers", Scientific Reports, vol. 5, Article No. 9866, May 8, 2015, pp. 1-7.

"Textile Transistors to Create Truly Wearable Electronics", Nano Werk, Retrieved on Jul. 31, 2018, Webpage availablz at : https://www.nanowerk.com/spotlight/spotid=1051.php.

"Flexible Graphene Electrodes Embedded in Textiles", Kurzweil, Retrieved on Jul. 31, 2018, Webpage available at : http://www.kurzweilai.net/flexible-graphene-electrodes-embedded-in-textiles.

"Feasibility Study of yARns and fabrics with ANNexed Electronic Functions", Arianne, Retrieved on Jul. 31, 2018, Webpage available at : http://www.diee.unica.it/eolab/arianne/.

Yun et al., "Ultrasensitive and Highly Selective Graphene-Based Single Yarn for Use in Wearable Gas Sensor", Scientific Reports, vol. 5, Article No. 10904, Jun. 4, 2015, pp. 1-7.

Extended European Search Report received for corresponding European Patent Application No. 16155639.4, dated Aug. 4, 2016, 6 pages.

International Search Report and Written Opinion received for corresponding Patent Cooperation Treaty Application No. PCT/FI2017/050084, dated Apr. 24, 2017, 13 pages.

* cited by examiner

141

141

141

APPARATUS AND METHOD OF FORMING AN APPARATUS COMPRISING TWO DIMENSIONAL MATERIAL

RELATED APPLICATION

This application was originally filed as PCT Application No. PCT/FI2017/050084 filed Feb. 14, 2017, which claims priority benefit from EP Patent Application No. 16155639.4 filed Feb. 15, 2016.

TECHNOLOGICAL FIELD

Example of the disclosure relate to an apparatus and method of forming an apparatus comprising a two dimensional material. In particular, they relate to an apparatus and method of forming an apparatus comprising a two dimensional material which may be arranged to sense one or more parameters.

BACKGROUND

Apparatus comprising two dimensional materials such as graphene are known. Such apparatus may require electrical connections to be made to the two dimensional material to enable the apparatus to function as a sensor or other type of device.

It is useful to provide improved methods and apparatus for forming the apparatus and providing electrical connections to the two dimensional material.

BRIEF SUMMARY

According to various, but not necessarily all, examples of the disclosure, there may be provided a method comprising: transferring a layer of two dimensional material from a liquid surface onto a layer of woven electronic fabric; wherein the woven electronic fabric comprises a plurality of conductive strands and a plurality of non conductive strands such that the layer of two dimensional material and woven electronic fabric form a sensor.

In some examples the two dimensional material may comprise graphene. The graphene may be functionalized with at least one of; colloidal quantum dots, metallic nanoparticles, bio-functional molecules.

In some examples the two dimensional material may be transferred to the woven electronic fabric by capillary action.

In some examples the two dimensional material may be suspended between strands of the woven electronic fabric.

In some examples the method may comprise providing a filler material between strands of woven electronic fabric. The filler material may be configured to be transparent to a parameter that is to be sensed by the two dimensional material. The filler material may comprise a dielectric.

In some examples the method may comprise providing a further layer of woven electronic fabric overlaying the two dimensional material.

In some examples the layers of woven electronic fabric may be magnetized.

In some examples the method may comprise providing at least one layer of woven electronic fabric on a backing substrate. The method may comprise providing read out electronics on the backing substrate.

In some examples the woven electronic fabric may comprise parallel conductive strands.

In some examples the woven electronic fabric may comprise perpendicular conductive strands.

In some examples the method may comprise providing a protective polymer layer overlaying the layer of two dimensional material.

In some examples the method may comprise providing a further substrate overlaying the protective polymer layer.

According to various, but not necessarily all, examples of the disclosure, there may be provided an apparatus comprising: a layer of two dimensional material supported by a layer of woven electronic fabric; wherein the woven electronic fabric comprises a plurality of conductive strands and a plurality of non conductive strands such that the layer of two dimensional material and woven electronic fabric form a sensor.

In some examples the layer of two dimensional material may be transferred to the layer of woven electronic fabric from a liquid surface.

In some examples the two dimensional material may comprise graphene. The graphene may be functionalized with at least one of; colloidal quantum dots, metallic nanoparticles, bio-functional molecules.

In some examples the two dimensional material may be transferred to the woven electronic fabric by capillary action.

In some examples the two dimensional material may be suspended between strands of the woven electronic fabric.

In some examples the apparatus may comprise a filler material between strands of woven electronic fabric. The filler material may be configured to be transparent to a parameter that is to be sensed by the two dimensional material. The filler material may comprise a dielectric.

In some examples the apparatus may comprise a further layer of woven electronic fabric overlaying the two dimensional material.

In some examples the layers of woven electronic fabric may be magnetized.

In some examples the apparatus may comprise at least one layer of woven electronic fabric on a backing substrate. The apparatus may comprise read out electronics on the backing substrate.

In some examples the woven electronic fabric may comprise parallel conductive strands.

In some examples the woven electronic fabric may comprise perpendicular conductive strands.

In some examples the apparatus may comprise a protective polymer layer overlaying the layer of two dimensional material.

In some examples the apparatus may comprise a further substrate overlaying the protective polymer layer.

According to various, but not necessarily all, examples of the disclosure, there may be provided a sensor device comprising at least one apparatus as described above.

According to various, but not necessarily all, example of the disclosure there is provided examples as claimed in the appended claims.

BRIEF DESCRIPTION

For a better understanding of various examples that are useful for understanding the detailed description, reference will now be made by way of example only to the accompanying drawings in which.

Figure 4A:
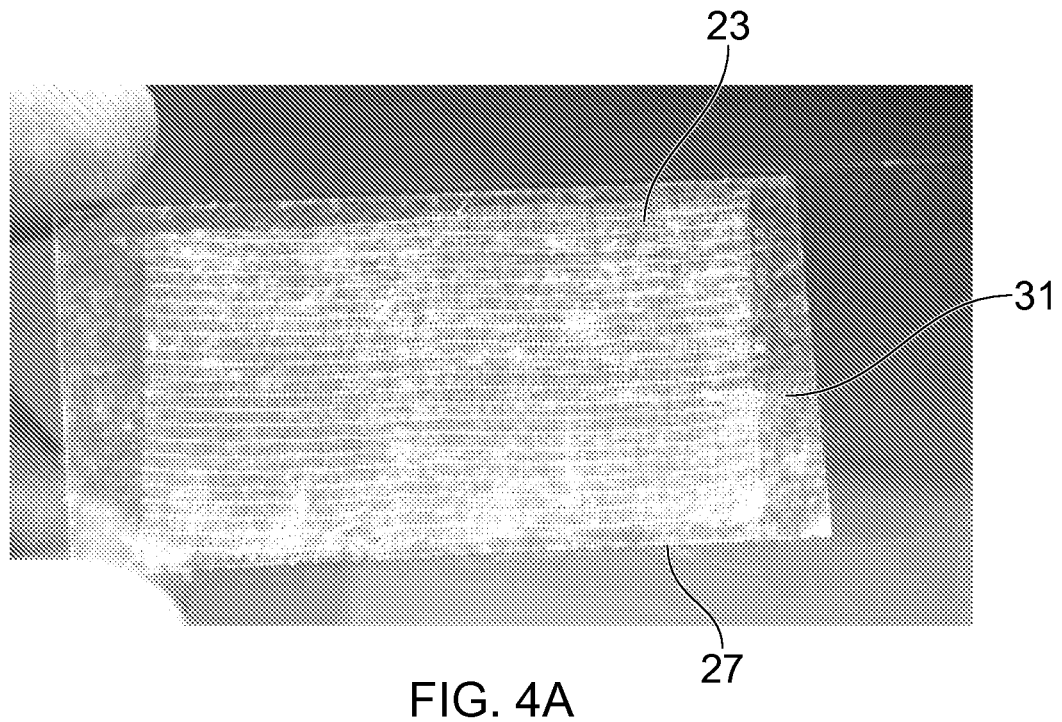
Figure 4B:
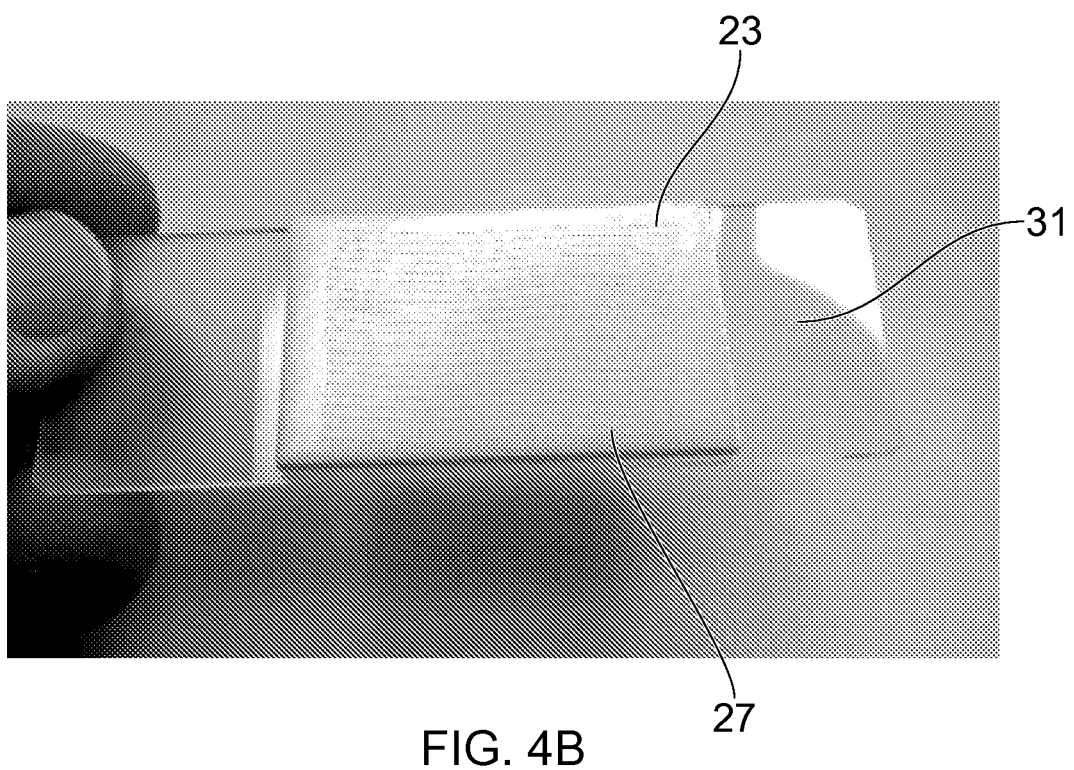
Figure 5A:
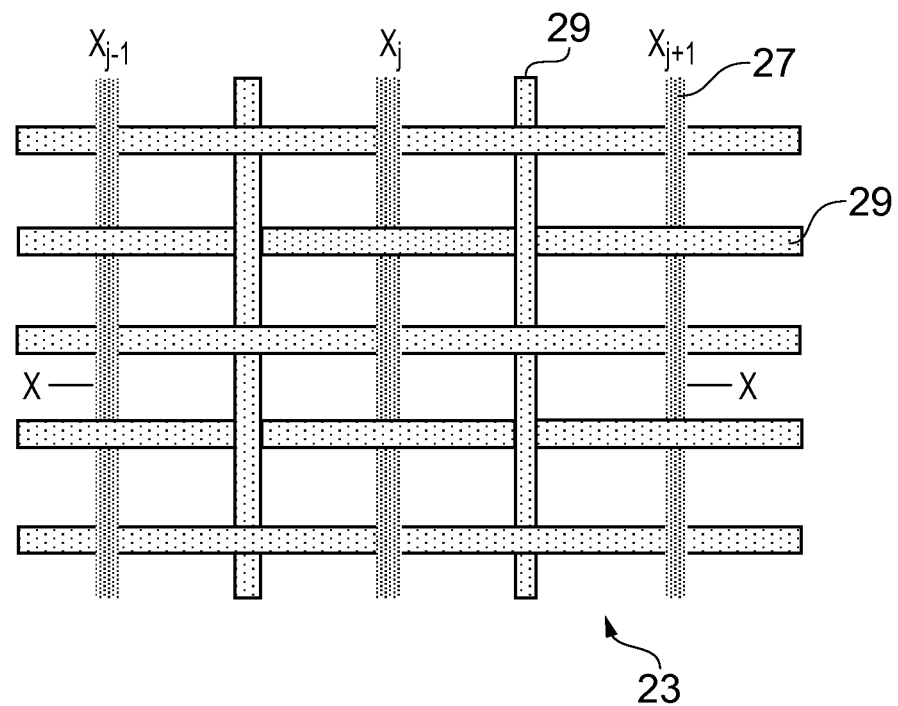
Figure 5B:
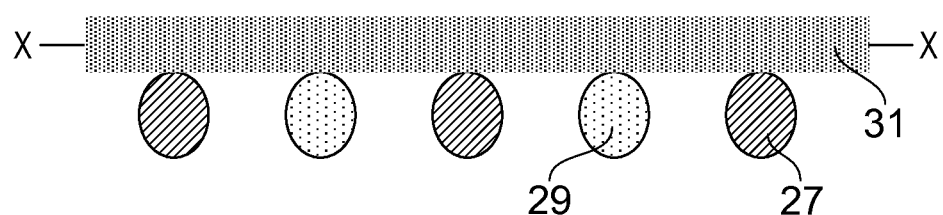
Figure 5C:
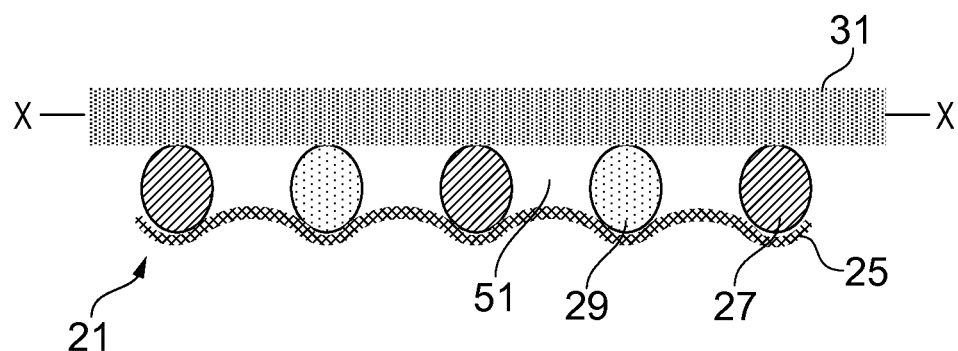
Figure 6A:
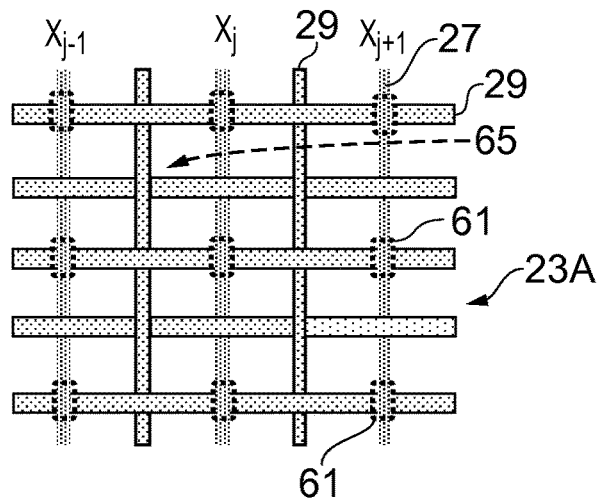
Figure 6B:
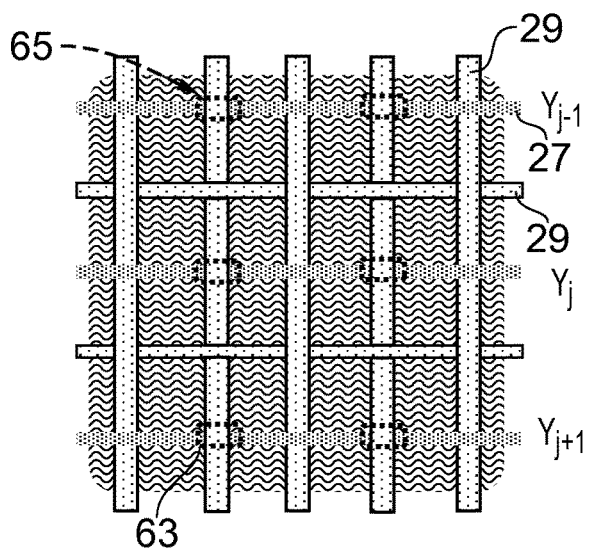
Figure 6C:
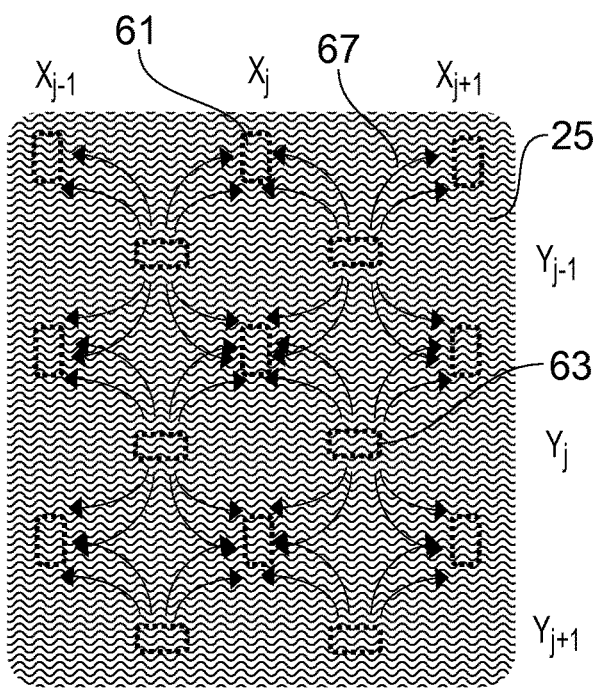
Figure 7:
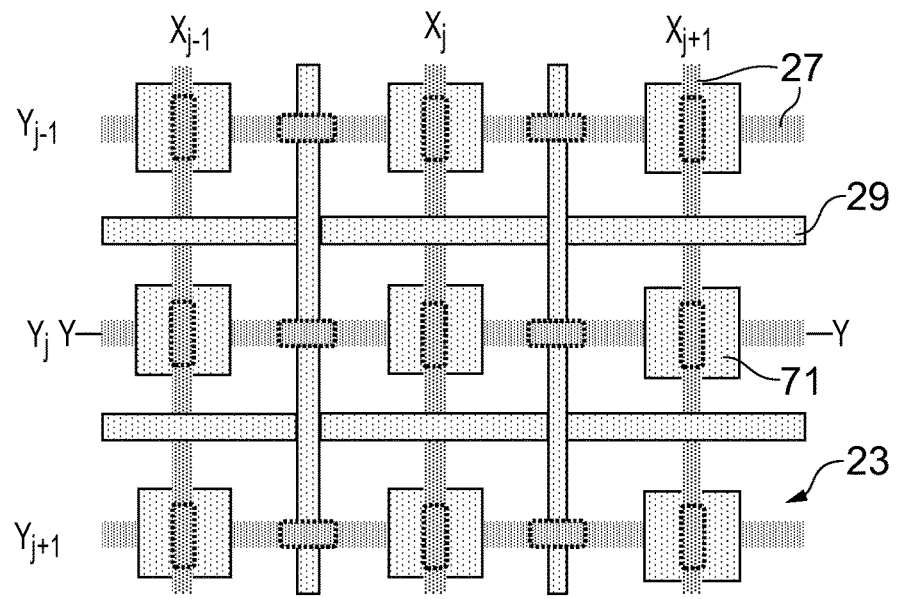
Figure 8A:
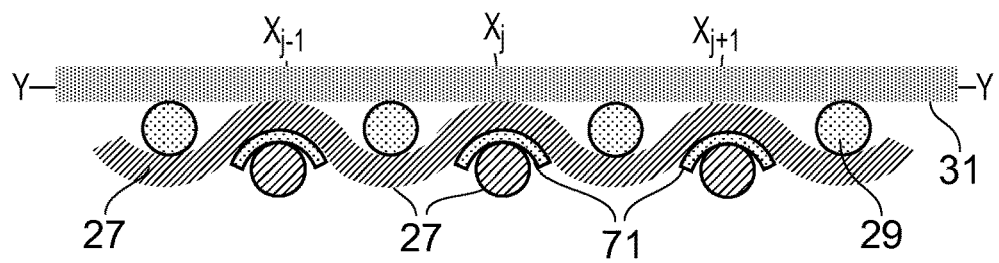
Figure 8B:
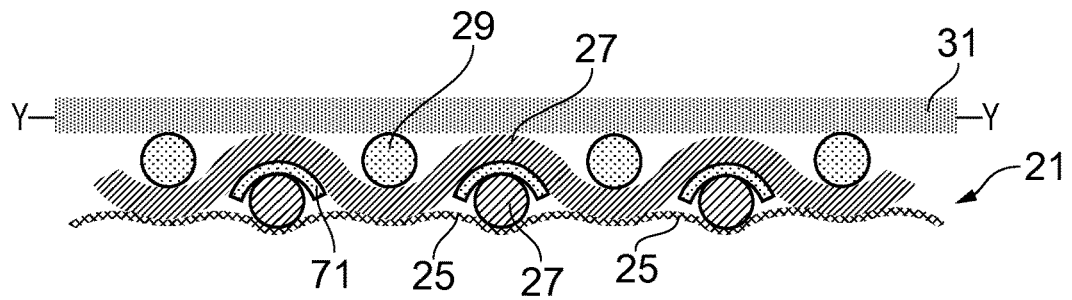
Figure 8C:
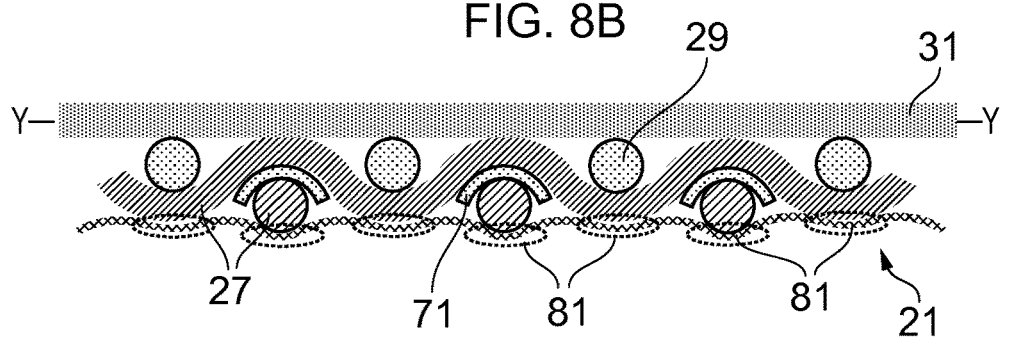
Figure 9A:
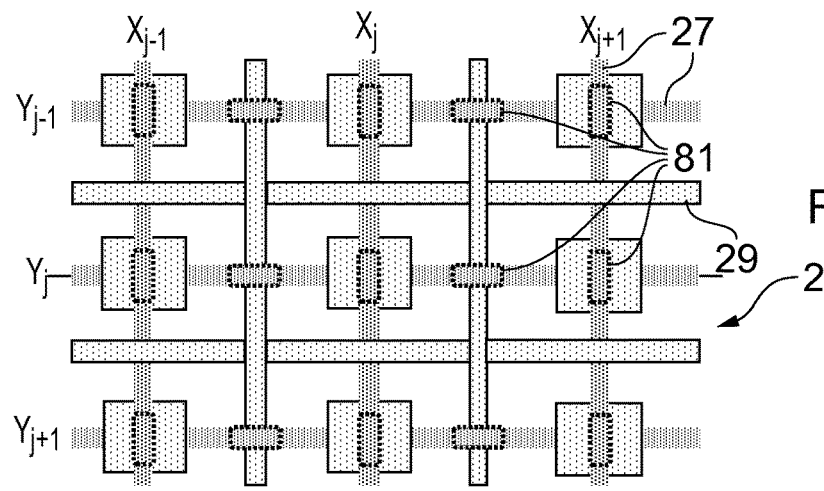
Figure 9B:
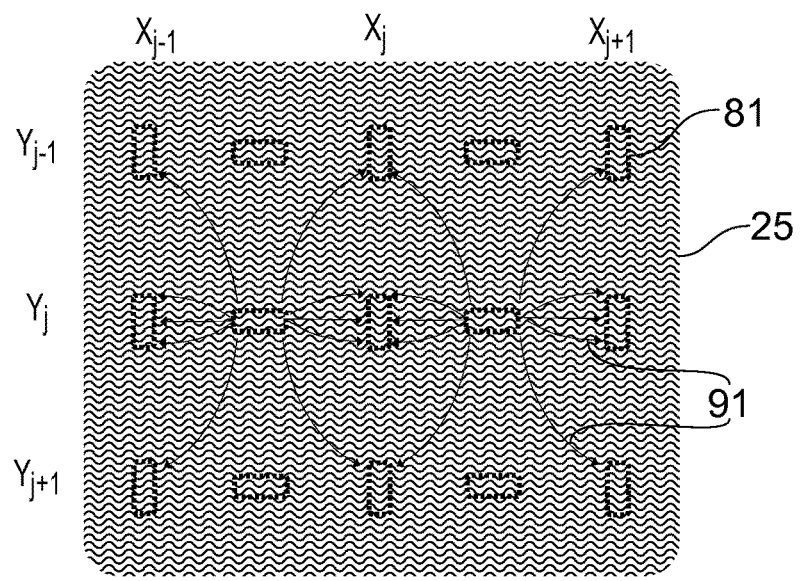
Figure 9C:
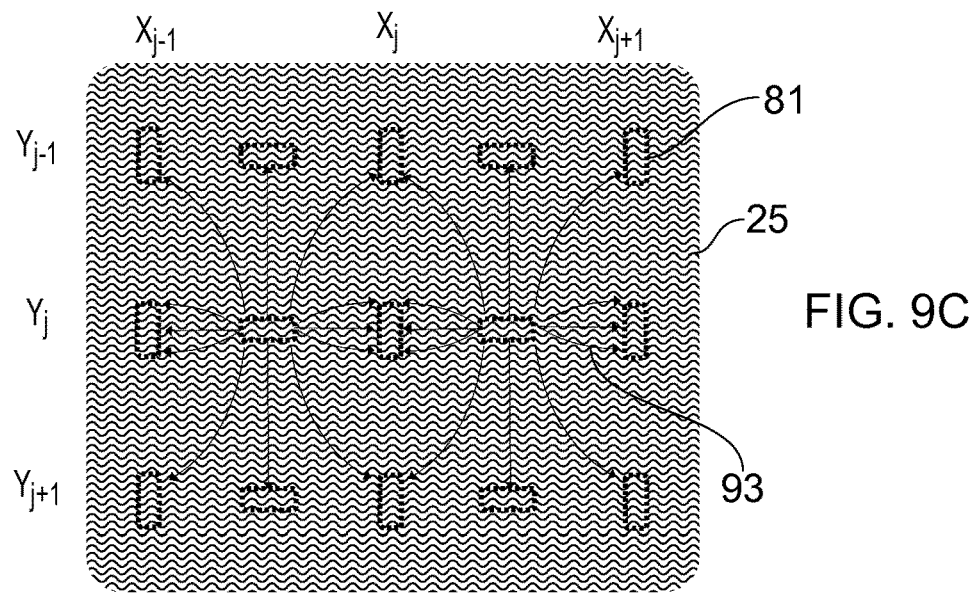
Figure 10A:
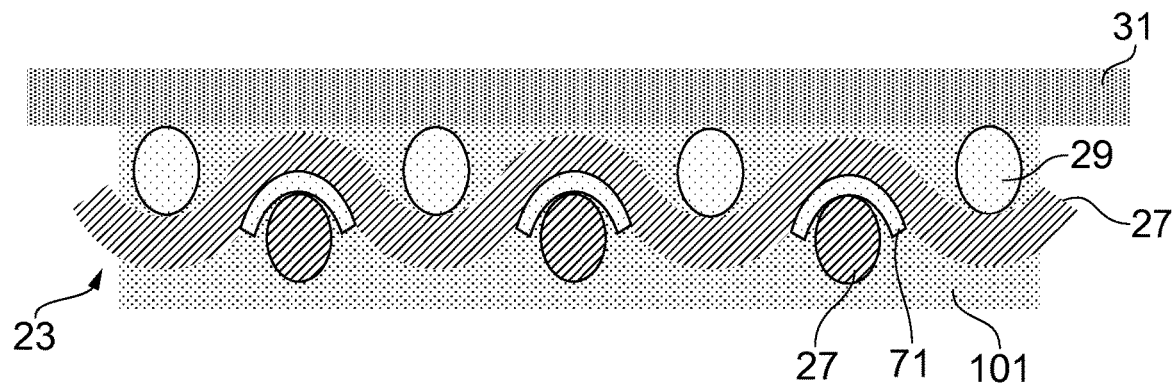
Figure 10B:
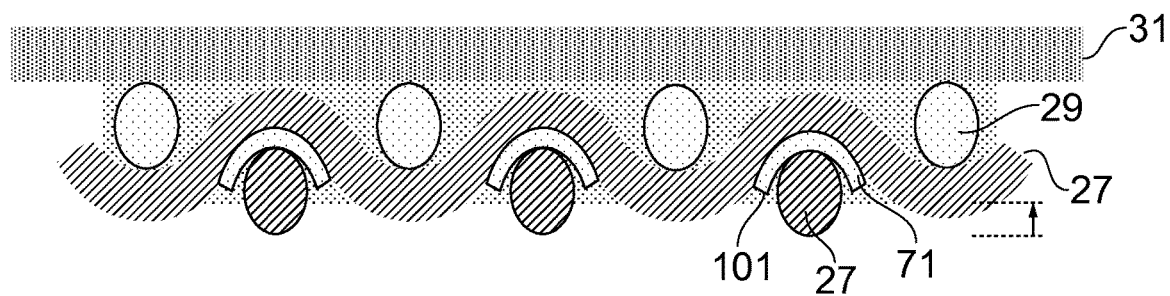
Figure 10C:
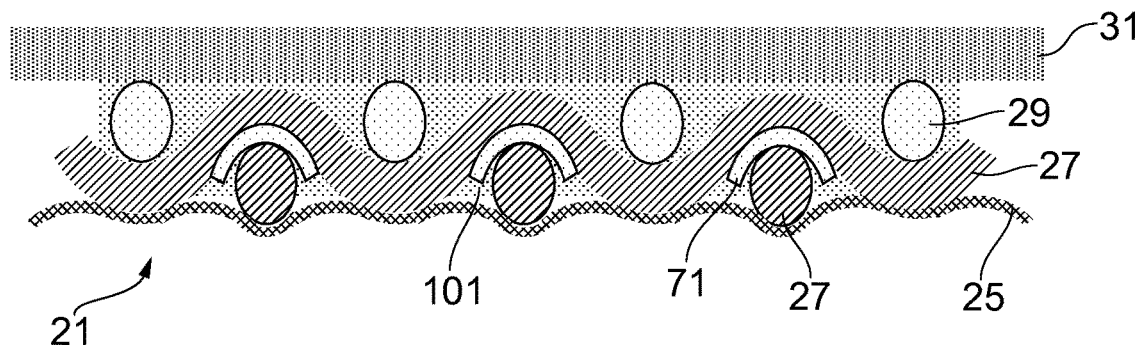
Figure 11A:
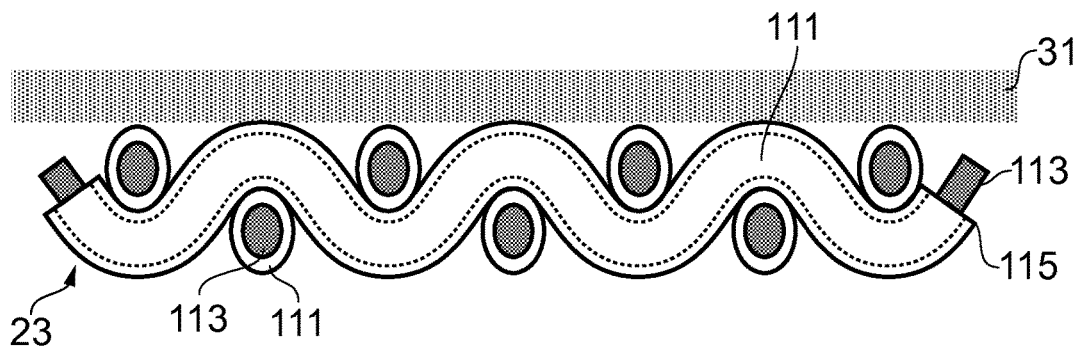
Figure 11B:
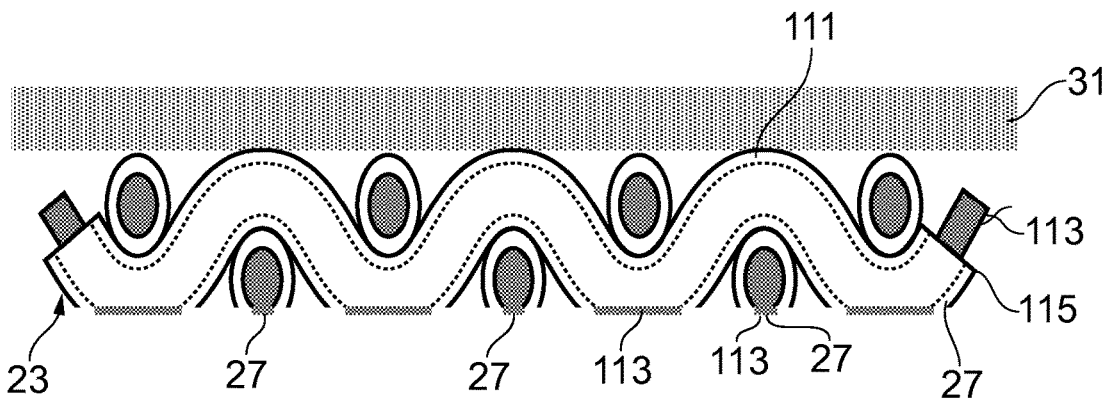
Figure 11C:
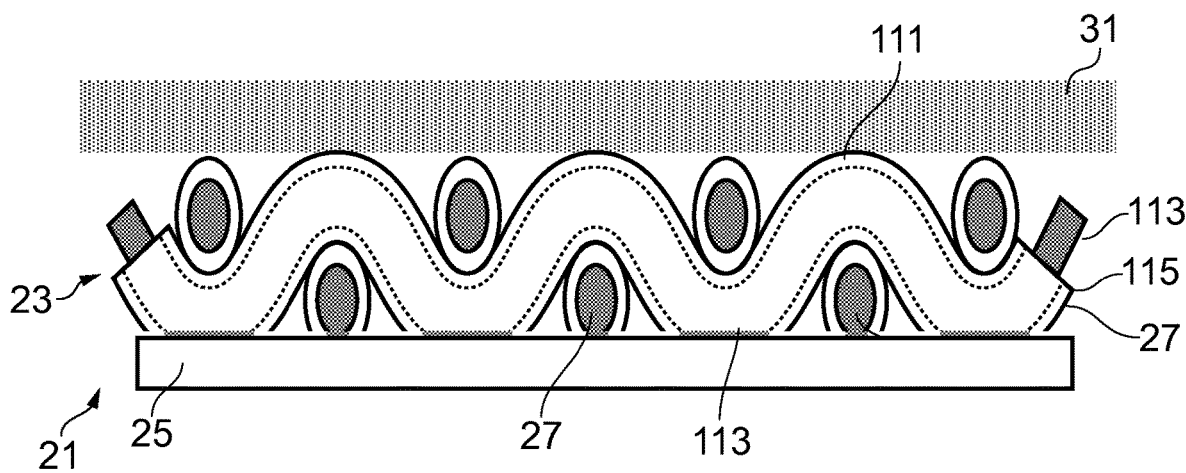
Figure 12A:
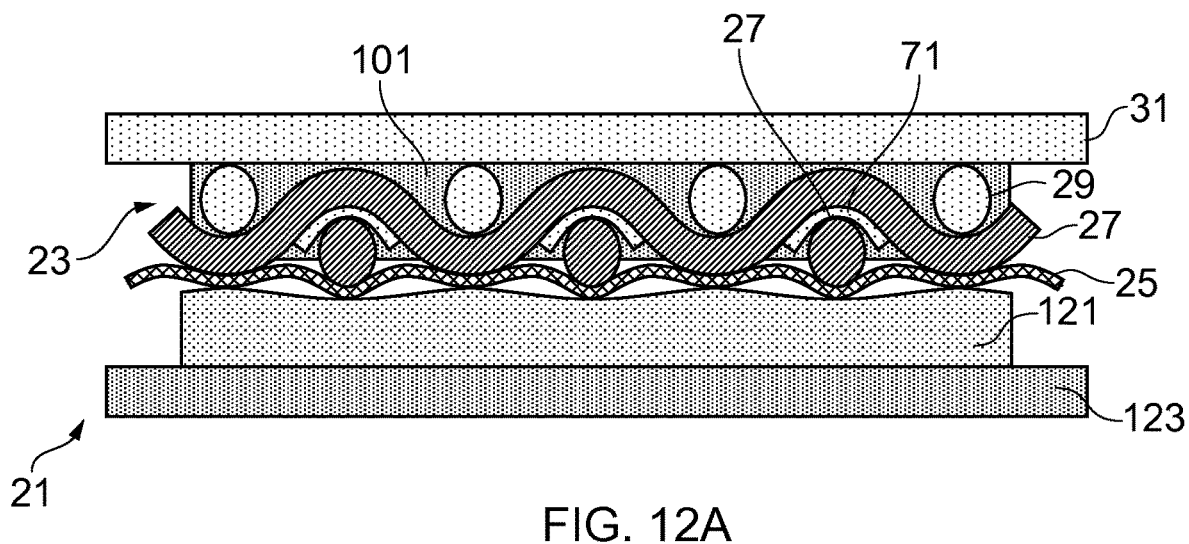
Figure 12B:
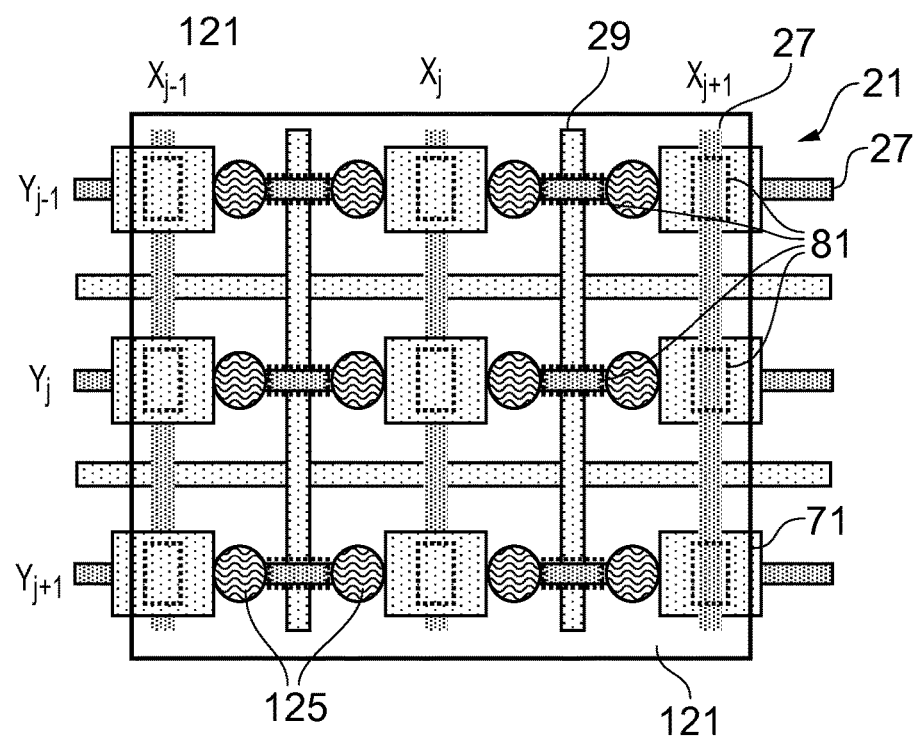
Figure 13:
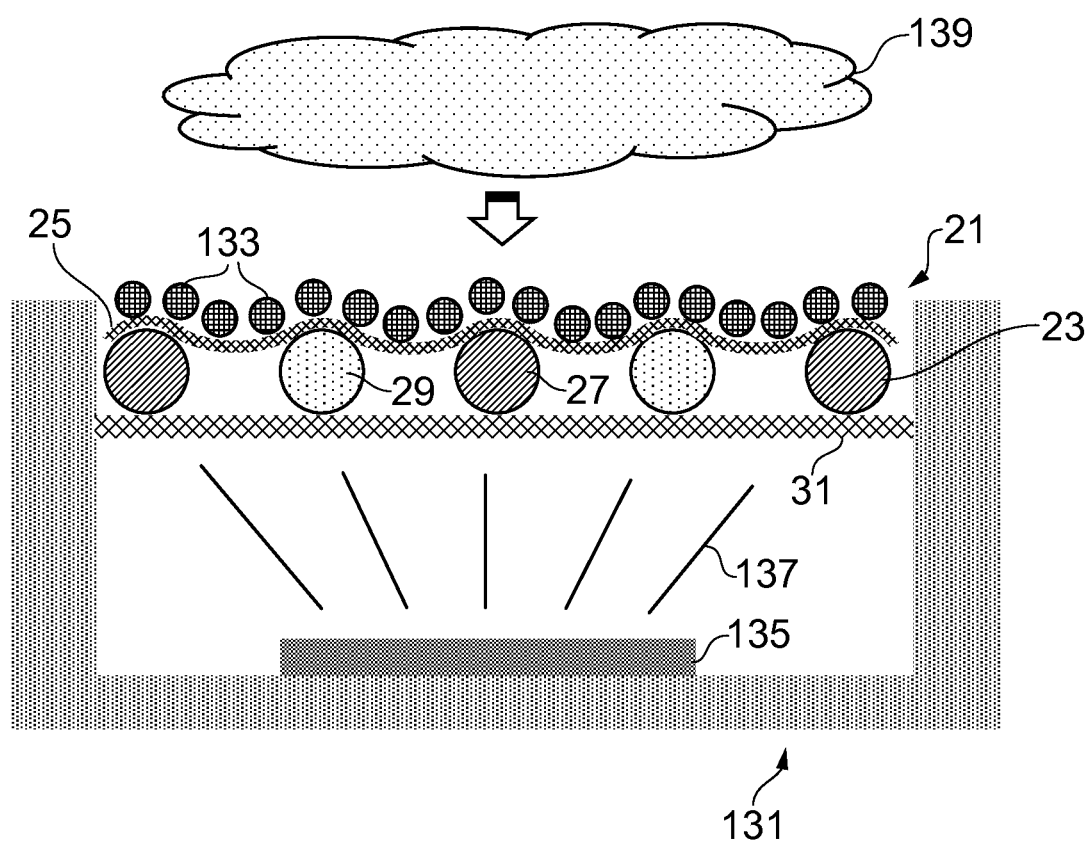

FIGS. 4A and 4B illustrate portions of example apparatus;
FIGS. 5A to 5C illustrate an example apparatus;
FIGS. 6A to 6C illustrate an example apparatus;
FIG. 7 illustrates an example woven electronic fabric;
FIGS. 8A to 8C illustrate example apparatus;
FIGS. 9A to 9C illustrate portions of an example apparatus;
FIGS. 10A to 10C illustrate another example apparatus;
FIGS. 11A to 11C illustrate another example apparatus;
FIGS. 12A and 12B illustrate another example apparatus;
FIG. 13 illustrates an example sensor device; and
FIGS. 14A to 14G illustrate example apparatus.

DETAILED DESCRIPTION

The figures illustrate a method and example apparatus 21 which may be formed using the example methods. The apparatus 21 may be for sensing. The apparatus 21 may comprise a layer of two dimensional material 25. The two dimensional material 25 may be arranged so that electrical properties of the two dimensional material 25 are dependent on a parameter that is to be sensed. The parameter could be a chemical or chemicals, radiation, temperature, or any other suitable parameter.

Figure 1:
FIG. 1 illustrates an example method.

FIG. 1 illustrates an example method according to examples of the disclosure. The method comprises, at block 1 transferring a layer of two dimensional material 25 from a liquid surface onto a layer of woven electronic fabric 23. The woven electronic fabric 23 comprises a plurality of conductive strands 27 and a plurality of non conductive strands 29 such that the layer of two dimensional material 25 and woven electronic fabric 23 form a sensor.

The two dimensional material 25 may be transferred from the liquid surface to the woven electronic fabric 23 by capillary action. The two dimensional material 25 may be transferred from the liquid surface to the woven electronic fabric 23 due to the negative pressure formed in the air pockets between the two dimensional material and the strands 27, 29 of the woven electronic fabric.

The layer of two dimensional material 25 may be wet when it is transferred to the woven electronic fabric 23. As the layer of two dimensional material 25 dries this pulls the layer of two dimensional material 25 into close contact with the strands 27, 29 of the woven electronic fabric 23. The layer of two dimensional material 25 may be held in place on the woven electronic fabric 23 by Van der Waals forces between the two dimensional material 25 and the strands 27, 29 of the woven electronic fabric 23

In some examples the apparatus 21 may be treated to increase the electronic contact between the layer of two dimensional material 25 and the conductive strands 27 within the woven electronic fabric 23. For instance in some examples, argon plasma treatment, or any other suitable treatment may be carried out to increase the electronic contact between the layer of two dimensional material 25 and the conductive strands 27 within the woven electronic fabric 23.

FIGS. 2 to 17 illustrate further example methods and example apparatus 21 that may be formed using examples of the disclosure.

Figure 2:
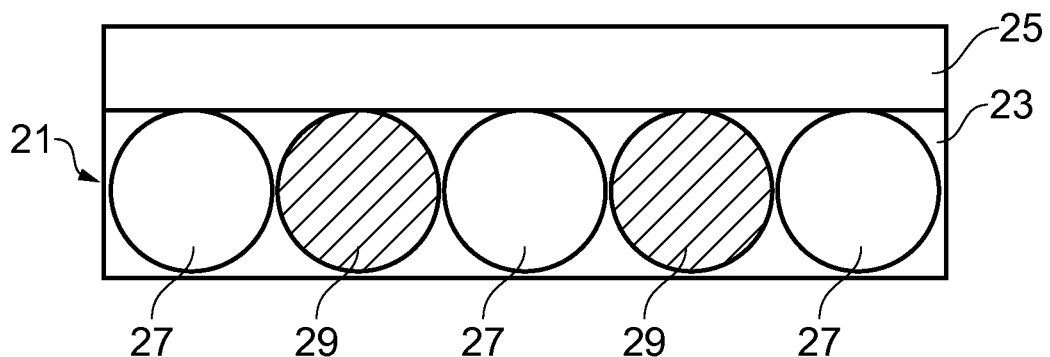
FIG. 2 illustrates an example apparatus.

FIG. 2 schematically illustrates a cross section through an example apparatus 21 according to examples of the disclosure. The example apparatus 21 comprises a layer of two dimensional material 25 supported by a layer of woven electronic fabric 23.

The layer of two dimensional material 25 may comprise a very thin layer of material. In some examples the layer of two dimensional material 25 could be an atomic monolayer. In some examples the layer of two dimensional material 25 could comprise several atomic monolayers. The layer of two dimensional material 25 could comprise graphene, molybdenum disulphide, tungsten disulphide, boron nitride or any other suitable material or combinations of these materials.

In some examples the layer of two dimensional material 25 may comprise functionalized graphene. The graphene could be functionalized using colloidal quantum dots, metallic nanoparticles, bio-functional molecules or any other suitable means. The means that is used to functionalize the graphene may depend on the parameter and/or parameters that the apparatus 21 is intended to sense.

The layer of two dimensional material 25 may be transferred to the surface of the woven electronic fabric 23 from the surface of a liquid. This may enable a sheet of two dimensional material to be transferred to the woven electronic fabric 23 without requiring any patterning of the layer of two dimensional material 25. This may reduce the defects that are introduced into the layer of two dimensional material 25 and may improve the efficiency of any devices which comprise the example apparatus 21.

The woven electronic fabric 23 comprises a plurality of conductive strands 27 and a plurality of non-conductive strands 29. In the example apparatus 21 of FIG. 2 both the conductive strands 27 and the non-conductive strands 29 extend parallel to each other. In the example of FIG. 2 the conductive strands 27 and the non-conductive strands extend into the page.

In some examples some of the conductive strands 27 may extend perpendicular to other conductive strands 27.

The conductive strands 27 may be arranged to provide an electrical connection to the layer of two dimensional material 25. The conductive strands 27 may comprise metal or any other suitable conductive material.

The non-conductive strands 29 may be provided between the conductive strands 27 within the woven electronic fabric 23. In the example of FIG. 2 at least one non-conductive strand 29 is provided between each pair of neighbouring conductive strands 27. This may prevent short circuits between the neighbouring conductive strands 27.

The conductive strands 27 may be configured to provide electrical connections to the two dimensional material 25 to enable the two dimensional material to function as a sensor. In some examples the conductive strands 27 may be arranged to provide a source electrode and drain electrode to the two dimensional material 25. In some examples the conductive strands 27 may be arranged to provide a plurality of source electrodes and drain electrodes to the two dimensional material 25. This may enable a plurality of sensors to be provided by the same layer of two dimensional material 24. In some examples the conductive strands 27 and the non-conductive strands 29 may be arranged to reduce cross talk between sensors provided on the same layer of two dimensional material 24. In some examples the conductive strands 27 may be arranged so that the two dimensional material provides a channel within a field effect transistor. Other types of sensors may be used in other examples of the disclosure.

Any suitable materials may be used for the conductive strands 27 and the non-conductive strands 29 of woven electronic fabric 23. Different materials may be used for the conductive strands 27 and the non-conductive strands 29. In some examples the conductive strands 27 may comprise a magnetic material such as a ferromagnetic material. The magnetic material may provide advantages in the construction, fabrication and functionality of the apparatus 1. For example magnetic conductive strands 27 may be pulled towards another magnetic portion within an apparatus which may improve the lamination of the apparatus 21 and the electrical connections between the conductive strands 27 and other conductive parts of the apparatus 21.

FIGS. 3A to 3D illustrate a method of forming an apparatus 21 according to some examples of the disclosure.

Figure 3A:
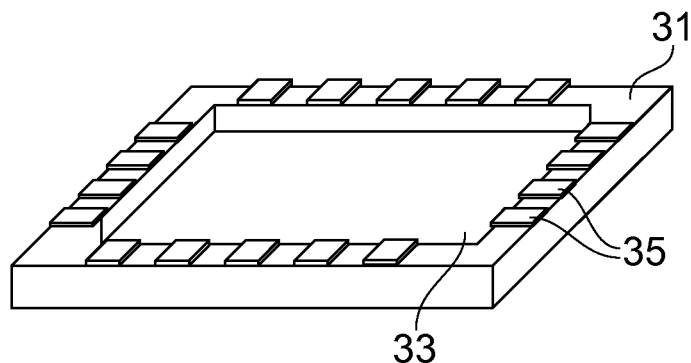
FIGS. 3A to 3D illustrate a method of forming an apparatus.

In FIG. 3A a backing substrate 31 is provided. The backing substrate 31 may comprise any means which may be configured to support the woven electronic fabric 23. The backing substrate 31 may comprise any suitable material. In some examples the backing substrate 31 may comprise a flexible material. In some examples the backing substrate 31 may comprise an insulating material.

In the example of FIG. 3A the backing substrate 31 comprises a recessed portion 33. The recessed portion 33 is arranged so that when the woven electronic fabric 23 is provided on the backing substrate 31 the woven electronic fabric 23 extends over at least a part of the recessed portion 33. The recessed portion 33 may be sized and shaped so as to ensure that air pockets are provided to enable the two dimensional material 25 to be transferred from the surface of the liquid to the woven electronic fabric 23.

A plurality of electrodes 35 are provided around the edge of the recessed portion 33. The electrodes 35 may be configured to provide electrical connections to the conductive strands 27 of the woven electronic fabric 23. The electrodes 35 may comprise metal or any other suitable conductive material. In some examples read out circuitry may also be provided on the backing substrate 31.

The read out circuitry may comprise any means suitable for obtaining signals from the matrix of conductive strands 27 within the woven electronic fabric 23. In some examples the read out circuitry may be arranged to read out sequentially from a plurality of sensors provided within the apparatus 21. In some examples mutual capacitive read-out methods may be used. This may enable existing read out chips to be used in examples of the disclosure.

Figure 3B:
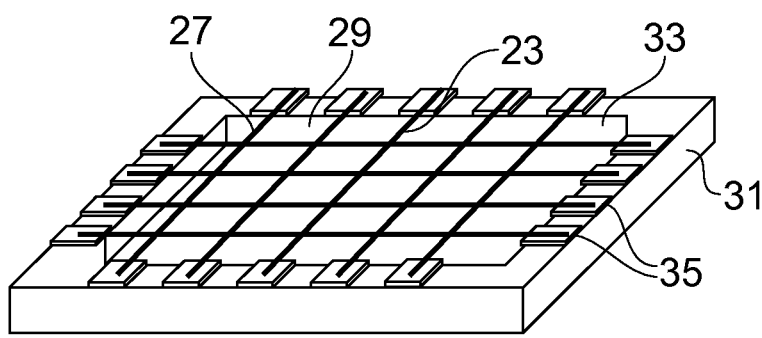

In FIG. 3B the woven electronic fabric 23 is attached to the backing substrate 31. The woven electronic fabric 23 comprises a plurality of strands 27, 29. The plurality of strands 27, 29 may comprise conductive strands 27 and non-conductive strands 29. The plurality of strands 27, 29 are arranged so that some of the strands 27, 29 extend horizontally across the recessed portions 33 and some of the strands 27, 29 extend vertically across the recessed portions 33.

The strands 27, 29 of the woven electronic fabric 23 are attached to the electrodes 35 of the backing substrate 31. The electrodes 35 may enable the strands 27, 29 of the woven electronic fabric 23 to be connected read out circuitry. Any suitable means may be used to attach the strands 27, 29 of the woven electronic fabric 23 to the substrate 31.

Figure 3C:
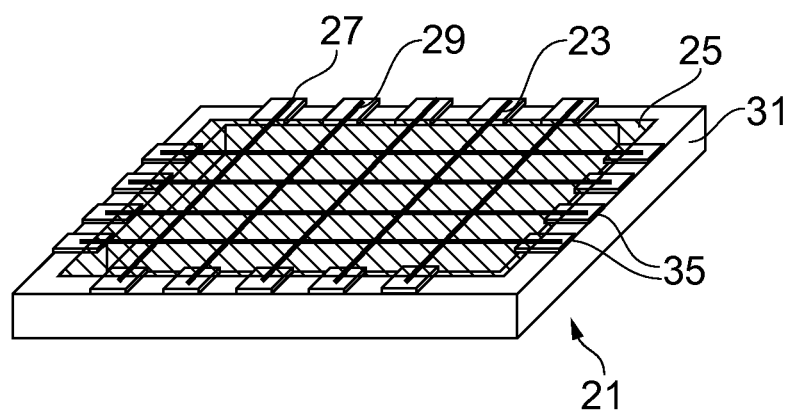

In FIG. 3C a layer of two dimensional material 25 is provided overlaying the woven electronic fabric 23. The layer of two dimensional material 25 may be transferred to the woven electronic fabric 23 from the surface of a liquid. The recessed portion 33 may ensure that air pockets are provided to transfer the two dimensional material 25 by capillary action.

The two dimensional material 25 may be transferred as a single continuous sheet. In some examples of the disclosure no patterning of the two dimensional material 25 may be needed. This may reduce defects within the two dimensional material 25 and may improve the efficiency of the apparatus 21.

In the example of FIG. 3C the two dimensional material 25 is supported by the woven electronic fabric 23 so that the two dimensional material 25 is suspended between strands of the woven electronic fabric 23. In other examples a filler material may be provided to support or at least partially support the two dimensional material 25 between strands of the woven electronic fabric 23.

Figure 3D:
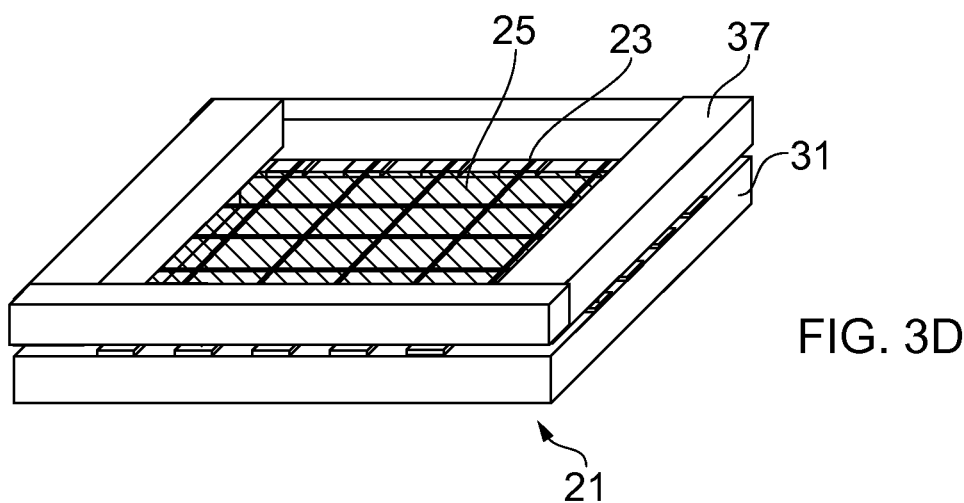

In FIG. 3D an additional substrate 37 is provided. The additional substrate 37 is arranged to laminate the woven electronic fabric 23 to the backing substrate 31.

In the example of FIG. 3D the additional substrate 37 is provided around the edge of the backing substrate 31. The additional substrate 37 is provided around the edge of the recessed portion 33. The additional substrate 37 is configured to laminate the edges of the layer of two dimensional material 25 to the electrodes 35. In the example of FIG. 3D the additional substrate 37 does not extend over the recessed portion 33. This ensures that the layer of two dimensional material 25 is exposed to the parameter that is to be sensed.

FIGS. 4A and 4B illustrate portions of an example apparatus 21 before the layer of two dimensional material 25 is attached. The apparatus 21 may comprise a layer of woven electronic fabric 23 which may be provided on a backing substrate 31. The backing substrate 31 may be as described above in relation to FIGS. 3A to 3D.

In the examples of FIGS. 4A and 4B the woven electronic fabric 23 comprises conductive strands 27 which extend horizontally. The conductive strands 27 extend from left to right in both FIG. 4A and FIG. 4B. It is to be appreciated that other arrangements of electronic fabric 23 may be used in other examples of the disclosure.

In both FIGS. 4A and 4B the apparatus 21 is provided on a backing substrate 31. In the example of FIG. 4A the backing substrate 31 comprises a brittle material such as glass. In the example of FIG. 4B the backing substrate 31 comprises a deformable material such as elastomeric foam. Other materials may be used for the backing substrate 31 in other examples of the disclosure.

FIGS. 5A to 5C schematically illustrate another example apparatus 21 according to examples of the disclosure.

FIG. 5A illustrates an example woven electronic fabric 23. The woven electronic fabric 23 comprises a plurality of conductive strands 27 and a plurality of non-conductive strands 29. In the example of FIG. 5A the conductive strands 27 extend vertically. Each of the conductive strands 27 extends parallel or substantially parallel to the other conductive strands 27.

In the example of FIG. 5A one non-conductive strand 29 is provided between each neighbouring pair of conductive strands 27 so that the fabric alternates between a conductive strand 27 and a non-conductive strand 29. In some examples more than one non-conductive strand 29 may be provided between each neighbouring pair of conductive strands 27. The woven electronic fabric 23 also comprises a plurality of non-conductive strands 29 which extend horizontally. The horizontal non-conductive strands 29 may extend perpendicular to or substantially perpendicular to the vertical conductive strands 27.

In the example of FIG. 5A only three conductive strands 27 of the woven electronic fabric are shown. It is to be appreciated that FIG. 5A shows only a section of the woven electronic fabric 23 and that more than three conductive strands 27 could be provided.

FIG. 5B illustrates a cross section through the woven electronic fabric 23 through the line X-X. FIG. 5B shows the alternating conductive strands 27 and non-conductive strands 29.

In the example of FIG. 5B the woven electronic fabric 23 has been attached to a backing substrate 31. The backing substrate 31 may provide support for the woven electronic fabric 23. The backing substrate 31 may comprise read out circuitry for the woven electronic fabric 23.

FIG. 5C illustrates another cross section through the woven electronic fabric 23 through the line X-X. In the example of FIG. 5C the layer of two dimensional material 25 has been added to the woven electronic fabric 23 to form an apparatus 21.

The woven electronic fabric 23 may be arranged so that an air gap 51 is provided between the strands 27, 29 of the woven electronic fabric 23. The air gap 51 may enable the layer of two dimensional material 25 to be transferred from the surface of a liquid to the woven electronic fabric 23 via capillary action. This may reduce the introduction of any defects into the layer of two dimensional material 25.

In the example of FIG. 5C the two dimensional material 25 is suspended between strands 27, 29 of the woven electronic fabric 23. In the example of FIG. 5C the two dimensional material 25 is suspended in air between the strands 27, 29 of the woven electronic fabric 23. The distance over which the two dimensional material 25 is suspended may depend on the grade of yarn that is used within the woven electronic fabric 23 and/or the tightness of the weave of the woven electronic fabric 23. In some examples the two dimensional material 25 may be suspended for a distance of tens of micrometers to several millimeters. This may reduce the introduction of impurities and defects into the two dimensional material 25. This may improve the efficiency of the apparatus 21.

In the previously illustrated examples the layer of two dimensional material 25 is provided overlaying a single layer of woven electronic fabric 23. FIGS. 6A to 6C schematically illustrate an example apparatus 21 in which the layer of two dimensional material 25 is laminated between two layers of woven electronic fabric 23.

FIG. 6A illustrates a first layer of woven electronic fabric 23A. The first layer of woven electronic fabric 23A comprises a plurality of conductive strands 27 and a plurality of non-conductive strands 29. In the example of FIG. 6A the conductive strands 27 and the non-conductive strands 29 are arranged in the same configuration as the example of FIG. 5A with a plurality of alternating conductive strands 27 and non-conductive strands 29 extending vertically and only non-conducting strands 29 extending horizontally. Other arrangements of the strands 27, 29 within the woven electronic fabric 23 may be used in other examples of the disclosure.

The dashed lines 61 indicate the areas where the conductive strands 27 make electronic contact with the two dimensional material 25. The electronic contacts may provide a path for direct current between the two dimensional material 25 and the conductive strands 27 within the first layer of woven electronic fabric 23A. The electronic contacts may be made at the locations where the conductive strands 27 are most elevated. This may be the areas where the conductive strands 27 pass over the non-conductive strands 29.

FIG. 6B illustrates a second layer of woven electronic fabric 23B. The second layer of woven electronic fabric 23B may be provided overlaying the first layer of woven electronic fabric 23A.

The second layer of woven electronic fabric 23B also comprises a plurality of conductive strands 27 and a plurality of non-conductive strands 29. In the example of FIG. 6B the conductive strands 27 and the non-conductive strands 29 are arranged in a similar configuration as the example of FIGS. 5A and 6A. However in the example of FIG. 6B the layer of woven electronic fabric 23B has been rotated through 90° relative to the first layer of woven electronic fabric 23A. The second layer of woven electronic fabric 23B comprises a plurality of alternating conductive strands 27 and non-conductive strands 29 extending horizontally and only non-conducting strands 29 extending vertically.

The dashed lines 63 indicate the areas where the conductive strands 27 of the second layer of woven electronic fabric 23 make electronic contact with the two dimensional material 25. The electronic contacts may provide a path for direct current between the two dimensional material 25 and the conductive strands 27 within the second layer of woven electronic fabric 23B. The electronic contacts may be made at the locations where the conductive strands 27 are most recessed. This may be the areas where the conductive strands 27 pass underneath the non-conductive strands 29.

When the apparatus 21 is assembled the second layer of woven electronic fabric 23B is provided overlaying the first woven electronic fabric 23A so that the vertical and horizontal strands 27, 29 of the two layers of woven electronic fabric 23A, 23B are aligned. In the example of FIGS. 6A to 6C the layers of woven electronic fabric are positioned so that the contact portions 63 of the second layer of woven electronic fabric 23B are positioned overlaying the non-conductive strands 29 of the first layer of woven electronic fabric 23A. The arrow 65 indicates the relative positions of the contact portions in the second layer of woven electronic fabric 23B and the non-conductive strands 29 in the first layer of woven electronic fabric 23A. This may enable the two layers of woven electronic fabric 23A, 23B to form a row and column matrix addressing system to a layer of two dimensional material 25.

FIG. 6C illustrates an example layer of two dimensional material 25 that may be provided between the two layers of woven electronic fabric 23A, 23B. The layer of two dimensional material 25 may be a continuous layer so that there is no patterning or discontinuities within the layer of two dimensional material 25.

The two dimensional material 25 may be transferred to the second layer of woven electronic fabric 23B from the surface of a liquid as described above. The second layer of woven electronic fabric 23B and the attached layer of two dimensional material 25 may then be laminated over the first layer of woven electronic fabric 23A so that contacts are simultaneously provided to both sides of the two dimensional material 25.

The areas at which the conductive strands 27 of the woven electronic fabric 23A, 23B contact the two dimensional material 25 are indicated by the dashed lines 61, 63 in FIG. 6C.

FIG. 6C also illustrates a plurality of arrows 67 which indicate the current paths when a voltage different is applied between the conductive strands 27 of the first layer of woven electronic fabric 23A and the conductive strands 27 of the second layer of woven electronic fabric 23B. It is to be appreciated that different current paths may be obtained by providing different voltage arrangements to the respective conductive strands 27.

In the example of FIGS. 6A to 6C two layers of woven electronic fabric 23 are used to provide a matrix of columns and rows for addressing the two dimensional material 25. FIG. 7 illustrates another example in which a single layer of woven electronic fabric 23 can be used to provide a matrix of columns and rows for addressing the two dimensional material 25.

In the example of FIG. 7 the woven electronic fabric 23 comprises a plurality of conductive strands 27 and a plurality of non-conductive strands 29. In the example of FIG. 7 the conductive strands 27 extend vertically and horizontally. The woven electronic fabric 23 comprises some conductive strands 27 that extend perpendicularly or substantially perpendicularly to other conductive strands 27.

In the example of FIG. 7 one non-conductive strand 29 is provided between each neighbouring pair of conductive strands 27 so that the fabric alternates between a conductive strand 27 and a non-conductive strand 29. In some examples more than one non-conductive strand 29 may be provided between each neighbouring pair of conductive strands 27. The alternating conductive strands 27 and non-conductive strands 29 extend in both the vertical and horizontal directions.

An insulator 71 is provided to prevent short circuits between overlaying conductive strands 27. The insulator 71 may comprise a dielectric material or any other suitable insulating material. In the example of FIG. 7 the insulator 71 is provided only in the regions where vertical conductive strands 27 pass over horizontal conductive strands 27 to separate the respective conductive strands 27.

FIGS. 8A to 8C illustrate a cross section of example apparatus 21 which comprises a layer of woven electronic fabric 23 as illustrated in FIG. 7. The cross section may be taken through the line Y-Y as indicated in FIG. 7.

FIG. 8A shows the alternating conductive strands 27 and non-conductive strands 29 which extend vertically within the woven electronic fabric 23. FIG. 8A also shows a conductive strand 27 which extends horizontally across the woven electronic fabric 23. The horizontal conductive strand 27 is woven between the vertical conductive strands 27 and vertical non-conductive strands 29. In the section of the woven electronic fabric 23 shown in FIG. 8A the horizontal conductive strands 27 pass over the vertical non-conductive strands 29 and underneath the vertical conductive strands 27.

The woven electronic fabric 23 also comprises an insulator 71 between overlaying conductive strands 27. The insulator 71 may be arranged to prevent short circuits between the overlaying conductive strands 27. The insulator 71 may comprise a dielectric material or any other suitable insulating material.

In the example of FIG. 8A the woven electronic fabric 23 has been attached to a backing substrate 31. The backing substrate 31 may comprise any means which provide support for the woven electronic fabric 23. In some examples read out circuitry may be provided on the backing substrate 31.

In the example of FIG. 8B the layer of two dimensional material 25 has been added to the woven electronic fabric 23 to form an apparatus 21. As in previous examples the layer of two dimensional material 25 may be transferred to the woven electronic fabric from the surface of a liquid.

FIG. 8C illustrates the contact points 81 where the conductive strands 27 of the woven electronic fabric 23 contact the two dimensional material 25. The dashed lines in FIG. 8C indicate the contact points 81. In the example of FIGS. 8A to 8C both the horizontal and vertical conductive strands 27 contact the two dimensional material 25.

The contact points 81 may provide a direct current path between the two dimensional material 25 and the conductive strands 27. The contact points 81 may enable charge transfer between the conductive strands 27 and the two dimensional material 25. In some examples the contact points 81 may provide a galvanic connection between the two dimensional material 25 and the conductive strands 27.

FIGS. 9A to 9C illustrate portions of another example apparatus 21. FIG. 9A illustrates an example layer of woven electronic fabric 23. The layer of woven electronic fabric 23 may be the same as the example woven electronic fabric 23 in FIGS. 7 and 8A to 8C. The contact points 81 where the conductive strands 81 contact the two dimensional material are indicated by the dashed lines in FIG. 9A.

FIG. 9B illustrates an example layer of two dimensional material 25 that may be provided overlaying the layer of woven electronic fabric 23. The two dimensional material 25 may be transferred to the layer of woven electronic fabric 23 from the surface of a liquid as described above. The contact points 81 between the conductive strands 27 and the two dimensional material 25 are indicated by the dashed lines 81 in FIG. 9B.

FIG. 9B also illustrates a plurality of arrows 91 which indicate the current paths between different contact points. In the example of FIG. 9B the horizontal conductive strand $Y_i$ is driven with voltage and the other horizontal conductive strands $Y_{i-1}$ and $Y_{i+1}$ are floating. All of the vertical conductive strands 27 are held at ground potential.

FIG. 9C illustrates another example layer of two dimensional material 25 that may be provided overlaying the layer of woven electronic fabric 23. As in FIG. 9B the contact points 81 between the conductive strands 27 and the two dimensional material 25 are indicated by the dashed lines.

In the example of FIG. 9C a different voltage arrangement is provided to the woven electronic fabric 23. In the example of FIG. 9C the horizontal conductive strand $Y_i$ is driven with voltage and the other horizontal conductive strands $Y_{i-1}$ and $Y_{i+1}$ are held at ground potential. All of the vertical conductive strands 27 are also held at ground potential. The example voltage arrangement of FIG. 9C provides a more uniform current distribution around each contact point 81 compared to the arrangement used in FIG. 9B. It is to be appreciated that in other examples of the disclosure different current paths may be obtained by providing different voltage arrangements to the respective conductive strands 27.

FIGS. 10A to 10C illustrate a cross section through another example apparatus 21 according to examples of the disclosure.

In the example of FIG. 10A a layer of woven electronic fabric 23 is provided on a backing substrate 31. The layer of woven electronic fabric 23 may be as illustrated in FIGS. 7 to 8C and may comprise conductive strands 27 extending in both the horizontal and vertical directions. Other arrangements of the woven electronic fabric 23 may be used in other examples of the disclosure.

A filler material 101 is provided within the woven electronic fabric 23. The filler material 101 is provided between the strands of the woven electronic fabric 23. In the example of FIG. 10A the filler material 101 extends over the surface of the woven electronic fabric 23.

The filler material 101 may comprise a material which is permeable to the parameter that is to be sensed by the apparatus 21. For instance, in examples where the apparatus 21 is arranged to sense a chemical or gas the filler material 101 may be arranged to be permeable to the chemical or gas. In examples where the apparatus 21 is arranged to sense light or other types of electromagnetic radiation the filler material 101 may be arranged to be at least partially transparent to the light or other type of electromagnetic radiation.

In some examples the filler material 101 may comprise a dielectric material such as a polymer dielectric. The polymer dielectric may be easy to shape to enable the filler material 101 to be configured for use within an apparatus 21.

The filler material 101 may comprise a material which does not affect the conductivity or charge distribution within the layer of two dimensional material 25. In some examples the filler material 101 may comprise a layer of hexagonal boron nitride provided overlaying the filler material 101. Hexagonal boron nitride has a similar molecular structure to graphene. In examples where graphene is used as the two dimensional material 25 the hexagonal boron nitride may reduce disruptions and dislocations within the graphene.

In FIG. 10B the filler material 101 has been recessed back to expose parts of the surface of the woven electronic fabric 23. In the example of FIG. 10B the filler material 101 has been recessed back to expose parts of the conductive strands 27 of the woven electronic fabric 23. Any suitable method may be used to recess the filler material 101.

In FIG. 10C the layer of two dimensional material 25 is provided on the woven electronic fabric 23 to form an apparatus 21. The layer of two dimensional material 25 may be transferred to the woven electronic fabric 23 from the surface of a liquid as described above.

The filler material 101 may be recessed back so that the two dimensional material 25 can contact the conductive strands 27 of the woven electronic fabric 23. The filler material 101 may be provided at a level so that it provides support to the two dimensional material 25. The filler material 101 may provide support in areas where the two dimensional material 25 would otherwise be freely suspended between the strands 27, 29 of the woven electronic fabric 23. In such examples the filler material 101 may increase the robustness of the apparatus 21 and decrease the likelihood of the two dimensional material 25 tearing or being otherwise damaged.

It is to be appreciated that other ways of increasing the robustness of the apparatus 21 may be used in other examples of the disclosure. For instance, in some examples the woven electronic fabric 23 may be flattened before the two dimensional material 25 is transferred to the woven electronic fabric 23. The woven electronic fabric 23 may be flattened using any suitable technique such as lamination. The woven electronic fabric 23 may be flattened so that all of the strands 27, 29 of the woven electronic fabric 23 are level. This may reduce the area of two dimensional material 25 which is freely suspended which may increase the robustness of the apparatus 21.

FIGS. 11A to 11O illustrate another example apparatus 21 according to examples of the disclosure. In the example of FIG. 11A the woven electronic fabric 23 comprises a plurality conducting wires 113 provided within an insulating coating 111. The conducting wires could comprise silver or any other suitable conductive material. The insulating coating 111 may comprise any suitable insulating material.

The conducting wires 113 and insulating coating 111 are provided in a woven array comprising a plurality of horizontal strands and a plurality of vertical strands. The strands may be arranged into conductive strands 27 and non-conductive strands by selectively removing sections of the insulating coating 111.

FIG. 11A illustrates an example woven electronic fabric 23 before any of the insulating coating 111 is removed. The insulating coating extends around the entire circumference of the conducting wire 113.

In the example of FIG. 11A a section of the insulating coating 111 is removed from the end 115 of the conducting wire 113. This may enable the end of the conducting wire 113 to be connected to an electrode 35.

In the example of FIG. 11A the woven electronic fabric 23 is attached to a backing substrate 31. The backing substrate 31 may be as described above.

In the example of FIG. 11A sections of the insulating coating 111 have been removed to provide a plurality of conductive strands 27. The insulating coating 111 has been removed so that sections of the conductive wire 113 are exposed. This enables the exposed sections of the conductive wire 113 to contact the layer of two dimensional material 25.

The insulating coating 111 may be removed by grinding or any other suitable technique.

It is to be appreciated that the woven electronic fabric 23 may also comprise a plurality of non-conductive strands 29 which have not had their insulating 111 coating removed. The conductive strands 27 and non-conductive strands 29 may be arranged in any suitable configuration.

In the example of FIG. 11C a layer of two dimensional material 25 is transferred to the woven electronic fabric 23 to form an apparatus 21. The layer of two dimensional material 25 may be transferred from the surface of a liquid as described above. The layer of two dimensional material 25 is positioned so that an electrical connection is provided between the layer of two dimensional material and the exposed areas of the conductive wire 113.

FIGS. 12A and 12B illustrate another apparatus 21 according to examples of the disclosure.

FIG. 12A illustrates a cross section through an example apparatus 21 and FIG. 12B illustrates a plan view of the apparatus 21. The apparatus 21 comprises a backing substrate 31, a layer of woven electronic fabric 23, filler material 101 provided between the strands 27, 29 of the woven electronic fabric 23 and a layer of two dimensional material 25.

The woven electronic fabric 23 and the filler material 101 may be arranged as described above in relation to FIGS. 10A to 10C. Other arrangements of the filler material 101 and the woven electronic fabric 23 may be used in other examples of the disclosure.

The apparatus 21 in the examples of FIGS. 12A and 12B may be configured to provide additional support to the two dimensional material 25. The additional support 121 may reduce the strains within the two dimensional material 25. This may reduce the likelihood of damage to the two dimensional material 25. In some examples the additional support may reduce the strain on the two dimensional material 25 when the apparatus 21 is bent or flexed or otherwise deformed.

In the example of FIGS. 12A and 12B the apparatus 21 comprises a protective polymer 121 and a further substrate 123. The further substrate 123 is not shown in FIG. 12B.

The protective polymer 121 is provided overlaying the two dimensional material 25. The protective polymer 121 may comprise any suitable polymer material. In some examples the protective polymer 121 may comprise a dielectric or insulating material. This may reduce the interaction between the two dimensional material 25 and the protective polymer 121.

In some examples the protective polymer 121 may comprise a flexible material. This may enable the apparatus 21 to be bent or otherwise deformed by a user.

The further substrate 123 is provided overlaying in the protective polymer 121. The further substrate 123 may comprise any suitable material. In some examples the further substrate 123 may comprise a flexible material which may enable the apparatus 21 to be bent or otherwise deformed by a user.

The protective polymer 121 and the further substrate 123 may be configured so that the two dimensional material 25 is positioned in a neutral axis within the layers of the apparatus 21. The thickness of the layers of the protective polymer 121 and the further substrate 123 may be selected so that the two dimensional material 25 is provided in the neutral axis. The neutral axis may be an axis within the apparatus 21 which is exposed to the minimal amount of strain when the apparatus 21 is bent or flexed or otherwise deformed. As the two dimensional material 25 is the most fragile part of the apparatus 21 having the two dimensional material 25 on the neutral axis reduces the likelihood of the two dimensional material 25 being damaged during use.

In the example of FIGS. 12A and 12B the protective polymer 121 and the further substrate 123 comprise gaps 125. The gaps 125 may be configured to enable the parameter that is to be sensed by the apparatus 21 to reach sections of the two dimensional material 25. The gaps 125 may be positioned so that they are provided between contact points 81 of the two dimensional material 25 and the conductive strands 27. The gaps 125 in the protective polymer layer 121 may prevent defects and impurities being introduced into the two dimensional material 25 in the region underneath the gaps 125. This may improve the efficiency of the apparatus 21.

The gaps 125 may be formed using any suitable technique. In some examples the gaps 125 may be formed by selectively removing the protective polymer 121 and the further substrate 123 from the desired locations within the apparatus 21. In some examples a solvent may be printed onto the protective polymer 121 and the further substrate 123 to remove the protective polymer 121 and the further substrate 123 from the desired locations. Other methods may be used in other examples of the disclosure.

In other examples, instead of providing gaps 125 the protective polymer 121 and the further substrate 123 may be arranged to be transparent to the parameter that is to be sensed by the apparatus 21. This may enable encapsulation of the apparatus 21 and may prevent contaminants from reaching the two dimensional material 25 and other parts of the apparatus 21.

It is to be appreciated that other configurations for increasing the robustness of the apparatus 21 may be used in other examples of the disclosure. For instance, in some examples a layer of hexagonal boron nitride may be provided on either side of the two dimensional material 25. For instance, where the two dimensional material 25 comprises graphene a hexagonal boron nitride-graphene-hexagonal boron nitride structure could be used. This may ensure that the two dimensional material 25 is provided within a neutral axis of a hexagonal boron nitride composite structure.

The hexagonal boron nitride composite structure may be formed using any suitable technique. In some examples a first layer of hexagonal boron nitride may be grown immediately on top of the two dimensional material. A layer of hexagonal boron nitride may be grown on top of a layer of graphene in a chemical vapour deposition reactor. A second layer of hexagonal boron nitride may then be deposited onto the other side of the two dimensional material after the two dimensional material has been released from the growth substrate before it is transferred to the woven electronic fabric 23. The second layer of hexagonal boron nitride may be deposited using techniques such as chemical vapour deposition or a solution process in which hexagonal boron nitride flakes are deposited from a volatile liquid using a thin-film coating method and/or other suitable techniques.

In some examples the hexagonal boron nitride layers may be deposited so that they do not completely cover the layer of two dimensional material 25. This provides a porous layer of hexagonal boron nitride which may leave regions of the two dimensional material 25 exposed. This ensures that the parameter that is to be sensed can still reach the layer of two dimensional material 25.

FIG. 13 illustrates an example sensor device 131 which may incorporate one or more apparatus 21 as described above. The sensor device 131 also comprises a source 135 of electromagnetic radiation 137. The source 135 may be arranged to provide a pulse of electromagnetic radiation 137. The sensor device 131 may be arranged to use the pulse of electromagnetic radiation 137 to detect analytes within a sample 139.

In the example of FIG. 13 the two dimensional material 25 and the woven electronic fabric 23 may be arranged to provide one or more field effect transistors.

In the example sensor device 131 of FIG. 13 quantum dots 133 are coupled to the layer of two dimensional material 25. The quantum dots 133 may be coupled to the channels of the field effect transistors. In the example of FIG. 13 the quantum dots 133 are provided overlaying the two dimensional material 25. In other examples the quantum dots 133 may be provided within and/or adjacent to the two dimensional material 25.

The quantum dots 133 may comprise a nanocrystal in which there is quantum confinement in all three dimensions. The quantum dots 133 may comprise any suitable material. The material that is used for the quantum dots 133 may be chosen dependent upon the analytes that are to be detected, the parameters of the pulse of electromagnetic radiation 137 or any other suitable factor. In some examples the quantum dots 133 may comprise lead sulphide, cadmium sulphide, cadmium selenide, germanium, lead selenide, lead telluride or any other suitable material.

The quantum dots 133 may be positioned within the apparatus 21 so that the pulse of electromagnetic radiation 137 is incident on the quantum dots 133. The quantum dots 133 may convert the incident pulse of electromagnetic radiation 137 into electrical charge. The changes in charge distribution within the quantum dots 133 may be detected by the transistors formed from the two dimensional material which then produces a measurable electrical response.

In some examples the quantum dots 133 may generate excitons in response to the pulse of electromagnetic radiation 137. The excitons may be separated into electron-hole pairs and either the holes or electrons are removed by the two dimensional material 25. This provides a doping effect in the two dimensional material 25 so that the output of a transistor within the apparatus 21 is indicative of the charges generated by the quantum dots 133.

In some examples a ligand may be coupled to the quantum dots 133. The ligand may be provided on the surface of the quantum dots 133. The ligand may affect charge transfer between respective quantum dots 133 and/or between quantum dots 133 and the two dimensional material 25. In some examples the ligand may be arranged within the quantum dots 133 to maintain a separation distance between quantum dots 133. Different ligands may be used to provide different distances between quantum dots 133.

In some examples the ligand may be configured to connect the quantum dots 133 to each other. In some examples the ligand may be configured to connect the quantum dots 133 to the two dimensional material 25.

The ligand may comprise any suitable material. The material that is used for the ligand may be chosen dependent upon the analytes that are to be detected, the parameters of the pulse of electromagnetic radiation 137, the materials used for the quantum dots 133 or any other suitable factor. In some examples the ligand may comprise alkanedithiol, where the alkane comprises methane, ethane, propane, butane or any other suitable alkane, alkanethiol, amine such as butylamine, pyridine or any other suitable material.

The apparatus 21 is configured to be illuminated by a pulse of electromagnetic radiation 137. The pulse of electromagnetic radiation 137 may be provided by an source 135. In the example of FIG. 13 the source 135 is part of the sensing device 131. In other examples the source 135 may be provided separate to the apparatus sensing device 131. In such examples a waveguide or any other suitable means may be provided to direct the electromagnetic radiation 137 to the apparatus 21.

The pulse of electromagnetic radiation 137 may comprise any suitable type of electromagnetic radiation. In some examples the pulse of electromagnetic radiation 137 may comprise visible light, ultraviolet (UV) and/or infra red (IR) wavelength light or any other suitable wavelengths.

In some examples the source 135 may be configured to enable parameters of the pulse of electromagnetic radiation 137 to be controlled. The parameters of the pulse of electromagnetic radiation 137 may comprise wavelength, power duration of the pulse of electromagnetic radiation 137, pulse repetition frequency of electromagnetic radiation 137 or any other suitable parameter. This may enable a pulse of electromagnetic radiation 137 having particular parameters to be used to illuminate the apparatus 1. The values that are chosen for the parameters may depend on factors such as the material within the quantum dots 133, the ligands used, the analytes to be detected within the sample 139 or any other suitable factor.

In the example of FIG. 13 the sensing device 131 is exposed to a sample 139. In some examples the sensing device 131 may be positioned adjacent to a sample 139 or within a sample 139. In some examples the sample 139 may comprise a gas or other fluid which may be configured to flow over the sensing device 131.

The sample 139 may comprise one or more chemical analytes. The chemical analytes within the sample 139 may interact with the quantum dots 133 and/or ligands. This interaction may affect the time taken for charge transfer between the quantum dots 133 and the two dimensional material 25 when the electromagnetic radiation 137 is incident on the apparatus 21. The time taken for the charge transfer may increase or decrease depending on the materials and analytes involved.

When the apparatus 21 is illuminated with a pulse of electromagnetic radiation 137 the electromagnetic radiation 137 causes a change in charge distribution within the quantum dots 133. This causes a response to be provided by the transistors within the apparatus 21. The profile of the response provided by the transistors is dependent upon the time taken for charge transfer between the quantum dots 133 and the two dimensional material 25. The profile of the response provided by the transistor may comprise amplitude, response time constant, recovery time, recovery time constant or any other suitable parameter. When the apparatus 21 is exposed to a sample 139 the time taken for charge transfer between the quantum dots 133 and the two dimensional material 25 is dependent upon whether or not any analytes have interacted with the quantum dots 133 and/or ligand. Therefore the profile of the response provided by the apparatus 21 when an analyte is present is different to the response provided when the analyte is not present. This enables the response of the apparatus 21 to be used to provide an indication of the presence of an analyte. The profile of the output provided by the apparatus 21 can be processed to determine whether or not an analyte is present in the sample 139.

The example sensing device 131 could be used to enable chemicals to be classified without the need for chemical sampling. This may be used as a chemical nose or for any other suitable application. It is to be appreciated that other types of sensing devices 131 may be provided in other examples of the disclosure.

In some examples the sensing device 131 may be provided as a wearable device. In such examples the sensing device may be arranged to be positioned immediately adjacent to a user's skin or other parts of the users body. In such examples the sensing device 131 may be arranged to detect chemical on the surface of the user's skin which may provide an indication of the health or other conditions of the user.

FIGS. 14A to 14G illustrate example apparatus 21 being tested.

Figure 14A:
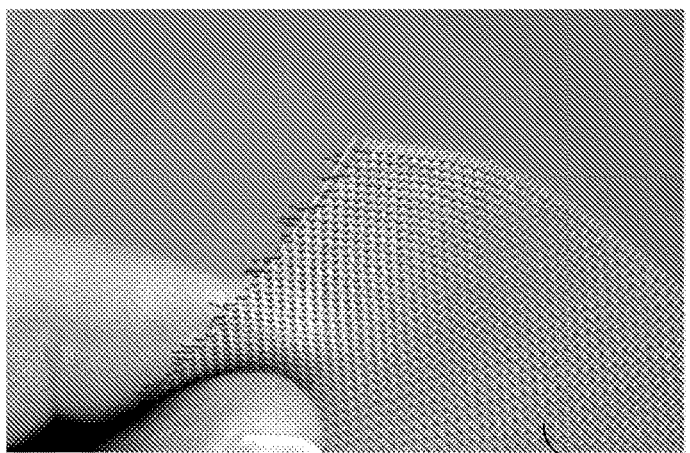
Figure 14B:
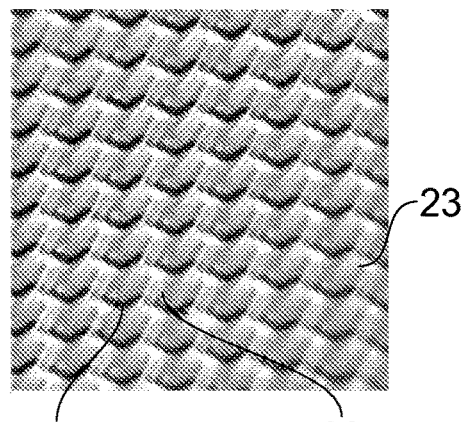

FIG. 14A is a photograph of an example woven electronic fabric 23 that may be used in some examples of the disclosure. FIG. 14B is a close up photograph of the same woven electronic fabric 23.

The woven electronic fabric 23 comprises conductive strands 27 and non-conductive strands 29 as described above. The conductive strands 27 are the darker strands in the photographs of FIGS. 14A and 14B. In the example of FIGS. 14A and 14B the conductive strands 27 only extend in the horizontal direction. Other arrangements of the strands 27, 29 may be used in other examples of the disclosure.

Figure 14C:
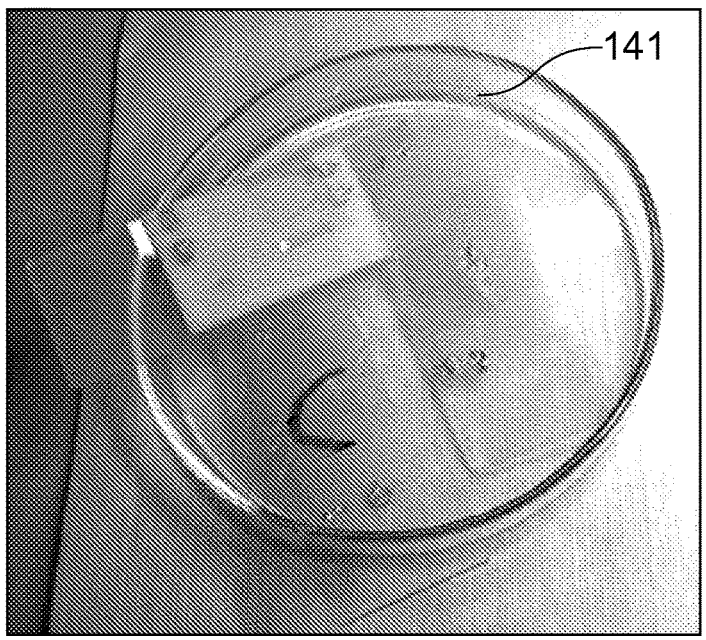
Figure 14D:
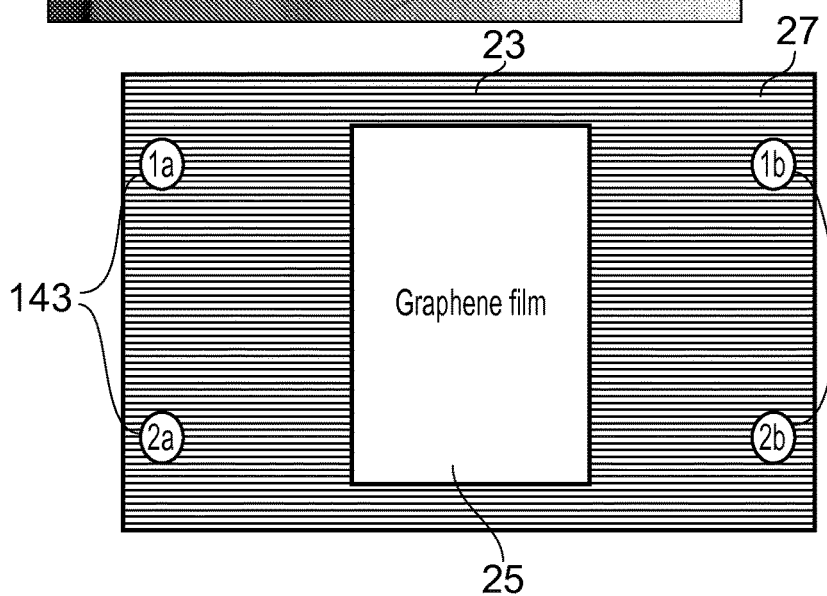

FIG. 14C is a photograph of example testing vehicles 141 that were used to test example apparatus 21. FIG. 14D schematically illustrates the structure of the testing vehicles 141. Each of the testing vehicles 141 comprises a layer of woven electronic fabric 23 mounted on a backing substrate 31. In one of the example testing vehicles 141 the woven electronic fabric 23 comprised copper conductive strands 27. In another example testing vehicle 141 the woven electronic fabric 23 comprised silver conductive strands 27. The conductive strands 27 only extend in the horizontal direction.

In the example testing vehicle 141 graphene was used as the two dimensional material 25. The graphene is provided overlaying a part of the woven electronic fabric 23. Electrical connections 143 were made to the conductive strands 27 to enable measurements to be obtained from the testing vehicles. The electrical connections 143 comprises silver paste.

In the examples of FIGS. 14C and 14D four electrical connections 143 were provided. The four electrical connections 143 were provided as an upper pair and a lower pair.

Figure 14E:
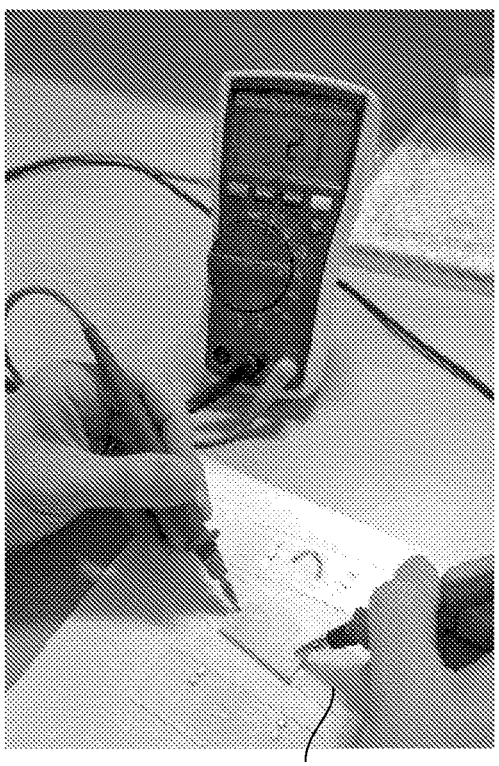
Figure 14F:
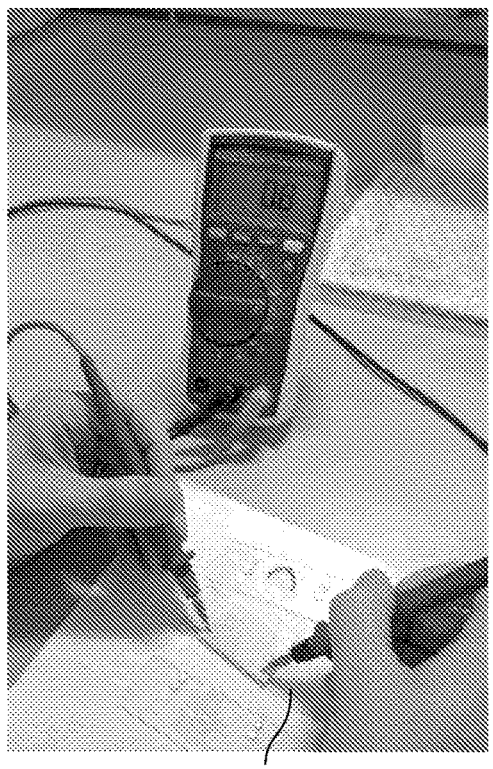
Figure 14G:
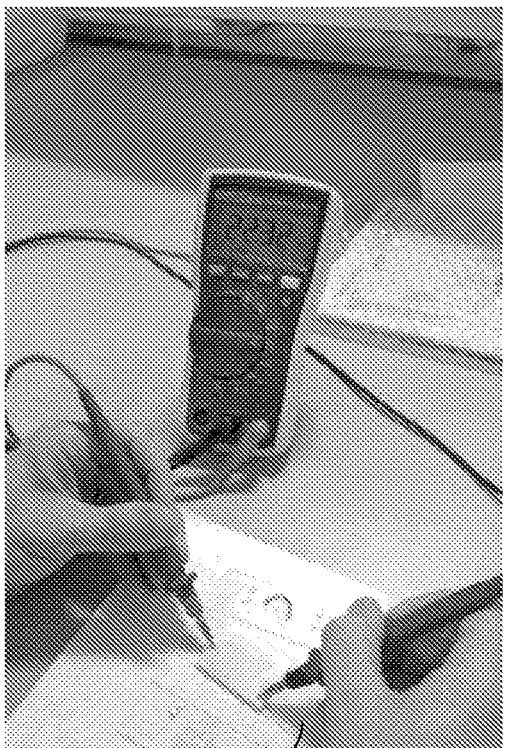

FIGS. 14E to 14G are photographs of conductance measurements being made using an example testing vehicle 141.

In the example of FIG. 14E the conductance measurements were made between the upper pair of the electrical connections 143. In the example of FIG. 14F the conductance measurements were made between the lower pair of the electrical connections 143. In the example of 14G the conductance measurements were made between one connection 143 from the upper pair of the electrical connections 143 and one connection 143 from the lower pair of electrical connections 143.

The measurements in the FIGS. 14E and 14F show that there was a low resistance between the upper pair of the electrical connections 143 and between the lower pair of the electrical connections 143. In the example measurements the resistance was in the range of a few Ohms. This provides an indication of good and stable conductivity along the conductive strands 27.

FIG. 14F shows the measurement of the resistance across the graphene. In the example measurements the resistance was in the range of 20 k Ohm. This provides an indication that the graphene is in good electrical contact with the conductive strands 27 of the woven electronic fabric 23.

Examples of the disclosure provide an apparatus 21 that can be used as sensing devices 131. As the apparatus 21 can be formed from un-patterned two dimensional materials this can provide an efficient sensing apparatus 21.

In some examples the two dimensional material 25 may be suspended between strands of the woven electronic fabric 23. This may also increase the efficiency of the apparatus 21 as it may reduce the defects and impurities that are added to the two dimensional material 21.

The apparatus 21 may be arranged to provide transistors. As the transistors are formed from a sheet of two dimensional material 25 the transistor may have a large surface area. This may reduce the noise level of the transistor and provide an improved sensing device 131.

Any number of transistors or other sensors can be provided within an apparatus 21. In some examples a large number of transistors could be provided. The large number of transistors could be used in a sensor array such as an electronic nose or any other suitable application. Examples of the disclosure may be useful in applications where high resolution is not needed such as in a chemical sensor.

In some examples the apparatus 21 may be provided within a wearable device. As the apparatus 21 is formed from a woven electronic fabric 23 the apparatus 21 may be flexible and lightweight so that it can be easily worn by a user. In some examples the woven electronic fabric 23 may be integrated into other fabric devices such as an item of clothing.

In some examples the woven electronic fabric 23 may be integrated into a sensor of other device that may be attached to the user's skin. As the device may be positioned close to the skin of the user this may be used to sense chemicals on the users skin such as chemicals in the user's sweat. In some examples the device may be used to provide an indication of the user's exposure to a chemical or other parameter.

The methods that are used to form the apparatus 21 may be scalable so that large numbers of the apparatus 21 may be formed.

The term "comprise" is used in this document with an inclusive not an exclusive meaning.

That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this detailed description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a features described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. A method comprising:
providing a layer of woven electronic fabric, the woven electronic fabric comprising a plurality of conductive strands and a plurality of non conductive strands such that a plurality of air gaps are formed between adjacent strands;
providing a layer of two dimensional material on a liquid surface;
overlaying the layer of two dimensional material with the layer of woven electronic fabric; and
using the plurality of air gaps to transfer the layer of two dimensional material from the liquid surface onto the layer of the woven electronic fabric;
wherein the layer of two dimensional material and the woven electronic fabric form a sensor; and
wherein the two dimensional material comprises graphene.

2. A method as claimed in claim 1 wherein the graphene is functionalized with at least one of: colloidal quantum dots, metallic nanoparticles, or bio-functional molecules.

3. A method as claimed in claim 1 wherein the two dimensional material is transferred to the woven electronic fabric by a capillary action.

4. A method as claimed in claim 1 wherein the transferred two dimensional material is suspended between strands of the woven electronic fabric.

5. A method as claimed in claim 1 further comprising providing a filler material between strands of the woven electronic fabric.

6. A method as claimed in claim 5 wherein the filler material is configured to be transparent to a parameter that is to be sensed by the two dimensional material.

7. A method as claimed in claim 5 wherein the filler material comprises a dielectric.

8. A method as claimed in claim 1 further comprising providing a further layer of woven electronic fabric overlaying the two dimensional material.

9. A method as claimed in claim 1 wherein the layers of the woven electronic fabric are magnetized.

10. A method as claimed in claim 1 further comprising providing at least one layer of woven electronic fabric on a backing substrate.

11. A method as claimed in claim 10 further comprising providing read out electronics on the backing substrate.

12. A method as claimed in claim 1 wherein the woven electronic fabric comprises at least one of: parallel conductive strands, or perpendicular conductive strands.

13. A method as claimed in claim 1 further comprising providing a protective polymer layer overlaying the layer of two dimensional material.

* * * * *